United States Patent [19]
Yano et al.

[11] Patent Number: 5,550,279
[45] Date of Patent: Aug. 27, 1996

[54] METHOD OF CONTROLLING REACTIONS

[75] Inventors: Takashi Yano; Hiroyuki Miura, both of Himeji, Japan

[73] Assignee: Daicel Chemical Industries, Ltd., Osaka, Japan

[21] Appl. No.: 431,461

[22] Filed: May 1, 1995

Related U.S. Application Data

[63] Continuation of Ser. No. 108,421, Aug. 19, 1993, abandoned.

[30] Foreign Application Priority Data

Aug. 20, 1992 [JP] Japan .................................. 4-245750

[51] Int. Cl.$^6$ .................................................. C07C 68/00
[52] U.S. Cl. .................................................. 558/277
[58] Field of Search ............................................ 558/277

[56] References Cited

FOREIGN PATENT DOCUMENTS

| | | |
|---|---|---|
| 0134668 | 3/1985 | European Pat. Off. . |
| 0460732 | 12/1991 | European Pat. Off. . |
| 04511129 | 4/1970 | Japan . |
| 60-58739 | 12/1985 | Japan . |
| 61-8816 | 3/1986 | Japan . |
| 61-43338 | 9/1986 | Japan . |
| 1287062 | 11/1989 | Japan . |
| 399041 | 4/1991 | Japan . |
| 942418 | 11/1968 | United Kingdom . |

*Primary Examiner*—Robert W. Romsuer
*Assistant Examiner*—Michael G. Ambrose
*Attorney, Agent, or Firm*—Cushman Darby & Cushman, L.L.P.

[57] ABSTRACT

In an exothermic liquid-phase reaction involving a liquid reactant and a gaseous reactant, the gas from the reactor vapor phase is subjected to gas-liquid separation and the non-condensible gas thus separated is recycled to the reactor liquid phase. As the non-condensible gas is recycled to the reactor liquid phase, the liquid components in the liquid phase are vaporized and the resulting latent heat of vaporization removes heat. Therefore, the reaction temperature can be easily controlled by regulating the flow rate of the non-condensible gas so recycled. This method of controlling the reaction temperature can be applied with particular advantage to a commercial process for producing a carbonic ester from an alcohol, carbon monoxide and oxygen.

14 Claims, 1 Drawing Sheet

METHOD OF CONTROLLING REACTIONS

This is a continuation of Application Ser. No. 08/108,421, filed on Aug. 19, 1993, now abandoned.

FIELD OF THE INVENTION

The present invention relates to a method of controlling the reaction temperature in liquid-phase reactions accompanied by the evolution of heat. The invention further relates to a method of producing carbonic esters which comprises allowing an alcohol to react with carbon monoxide and oxygen in a liquid phase.

BACKGROUND OF THE INVENTION

It is known that many of liquid-phase reactions using gaseous reactants are accompanied by the evolution of heat. As a technology for controlling the reaction temperature of such an exothermic liquid-phase reaction, it is common practice to provide the reactor with a cooling jacket or an internal coil for circulation of a cooling medium and adjust the temperature or flow rate of said cooling medium so as to control the reaction temperature. With this technology, it is difficult to control the reaction temperature when its change is sharp and abrupt and, moreover, the efficiency of heat removal is low. Particularly, when the reactor volume is large, it is difficult to control the reaction temperature efficiently.

As the exothermic liquid-phase reaction using a gaseous reactant, for example, Wacker oxidation, so-called oxo reaction, the reaction giving a carboxylic acid or carboxylic anhydride from an alcohol and/or its ester and carbon monoxide, and the reaction giving a carbonic ester from an alcohol, carbon monoxide and oxygen are known.

The technology for the production of carbonic esters, by which an alcohol is allowed to react with carbon monoxide and oxygen in a liquid phase, can be roughly classified into a process using a copper compound as the main catalyst and a process using a palladium compound as the main catalyst.

Processes using a copper compound as the main catalyst are described in Japanese Patent Publication No. 11129/1970 and Japanese Patent Publication No. 58739/1985. Because the catalytic activity of any copper compound is comparatively low, these processes require the use of a copper catalyst in a high concentration, e.g. the order of several moles/L (tens of % on a weight % basis), in order to realize a practically acceptable reaction rate. However, since this procedure entails the presence of active species oxidative divalent copper ions and chloride ions in high concentrations in the reaction system, not only the reactor body but also the instruments, piping, valves and other hardware exposed to the reaction mixture are subject to severe corrosion.

Processes using a palladium compound as the main catalyst are disclosed in Japanese Patent Publication Nos. 8816/1986 and 43338/1986 and Japanese Patent Laid-open No. 287062/1989. In these processes, a weak acid salt or halide of copper and a weak acid salt or halide of an alkali metal or alkaline earth metal are used as promoters. Since the catalytic activity of any palladium compound is high as compared with copper compounds, a sufficiently high reaction rate can be realized even when the amount of the palladium species is as small as about one-thousandth compared with the copper species used in the first-mentioned processes and the amount of divalent copper ions used concomitantly for reoxidation of palladium can also be reduced to about one-tenth to one-hundredth as compared with the first-mentioned processes. However, since the oxidative divalent palladium and divalent copper ions, which are catalyst active species, exhibit high oxidizing activity even at low concentration levels, the reactor and ancillary equipment are still exposed to highly corrosive conditions.

Several processes have so far been proposed for producing carbonic esters in the liquid phase with the aid of such catalysts.

By way of illustration, the specification of EP-A 134668 discloses a continuous process for producing a carbonic ester which comprises condensing the gas from the reactor vapor phase and recycling a portion of the condensed carbonic ester to the reactor to control the concentrations of water and alcohol in the reaction mixture at low levels, minimize the deactivation of the catalyst and prevent side reactions.

Japanese Patent Laid-open No. 99041/1991 discloses a continuous process designed for prevention of corrosion which comprises feeding an excess of carbon monoxide/oxygen-containing gas to the reactor, with-drawing the product carbonic ester, by-product water and unreacted alcohol as an azeotropic mixture, subjecting this vapor to gas-liquid separation and recovering the carbonic ester from the condensate. It is mentioned that, in this process, the non-condensible gas from gas-liquid separator may be returned to the reactor.

Furthermore, the specification of EP-A 460732 discloses a continuous process for producing dimethyl carbonate which, for an improved yield of the carbonic diester, comprises bubbling a carbon monoxide-containing gas through the reaction mixture to encourage the evaporation of methanol, water and dimethyl carbonate from the reaction mixture and recovering water and dimethyl carbonate from the resultant mixture gas, characterized in that the concentrations of methanol and water in the reaction mixture are controlled within specified ranges. In this process, the non-condensible gas containing a large proportion of carbon monoxide is recycled to the reactor.

In these conventional processes for producing carbonic esters, control of reaction temperature is generally carried out in the ordinary manner described hereinbefore, namely by the method of circulating a cooling medium through the reactor jacket or coil. Accordingly, the efficiency of heat removal is low and it is often difficult to control the reaction temperature. Moreover, since a corrosive catalyst is used for the reaction in these processes, an expensive corrosion-resistant material must be specified for the cooling coil and other hardware. Furthermore, in cases where the internal wall of the reactor is lined with a corrosion-resistant material such as glass and Teflon for added resistance to corrosion, passing a cooling medium through the jacket for cooling tends to cause cracks in the lining or a peeling thereof.

As an alternative technology for controlling the reaction temperature in the process for producing carbonic esters, a method is known which comprises cooling the reaction mixture in a heat exchanger and recycling it at a controlled temperature or flow rate. However, this method requires an additional capital expenditure for ancillary equipment. Moreover, it is essential that the circuit for the reaction mixture be made of an expensive corrosion-resistant material in order to prevent the corrosion by the catalyst in the reaction mixture. In addition, when the reaction mixture is circulated in this manner, the residence time is liable to vary so that the objective product cannot be obtained with good reproducibility.

In the prior art literature describing processes for producing carbonic esters, the concept of recycling a non-condensible gas to the reaction system is shown but the concept of controlling the reaction temperature by such recycling is not suggested.

Control of the reaction temperature in Wacker oxidation, oxo reaction, the reaction giving a carboxylic acid or carboxylic anhydride from an alcohol and/or its ester and carbon monoxide and the like has been also performed by the similar methods to those in said processes for procucing carbonic esters. Accordingly such problems as described above accompanying the reaction giving carbonic esters are also the case for above reactions.

SUMMARY OF THE INVENTION

Such being the circumstances, it is an object of the present invention to provide a method of controlling a reaction, which provides for an easy control of reaction temperature of an exothermic liquid-phase reaction using a gaseous reactant and for an effective utilizaiton of unreacted gaseous reactants.

It is another object of the invention to provide a method of controlling a reaction, which enables an efficient control of reaction temperature regardless of reactor volume.

It is a further object of the invention to provide a method of controlling a reaction, which provides for an easy control of reaction temperature with simple hardware and software even in the presence of a highly corrosive catalyst.

It is a still further object of the present invention to provide a method of producing a carbonic ester in good yield and with high steadiness.

The inventors of the present invention discovered, after a great research effort to accomplish the above-mentioned objects, that the reactor vapor phase can be easily separated into a gas and a liquid and that the reaction temperature can be easily controlled by recycling the non-condensible gas fraction to the reactor liquid phase.

The present invention, thus, provides a method of controlling a reaction in a liquid phase accompanied by evolution of heat and involving a liquid reactant and a gaseous reactant which comprises subjecting the gas from the reactor vapor phase to gas-liquid separation and recycling the non-condensible gas fraction to the reactor liquid phase to thereby control the reaction temperature.

As said exothermic liquid phase reaction, there may be mentioned Wacker oxidation, so-called oxo reaction, the reaction giving a carboxylic acid or a carboxylic anhydride from an alcohol and/or its ester and carbon monoxide, the reaction giving a carboxylic acid and a carboxylic anhydride from at least two members selected from among an alcohol, a dialkyl ether and an alkyl ester and carbon monoxide, the reaction giving a carbonic ester from an alcohol, carbon monoxide and oxygen, and so on.

The reaction temperature may be controlled by regulating the flow rate of the recycle gas.

The non-condensible gas may be compressed by a compressor and recycled to the reactor liquid phase. The non-condensible gas may be sparged through the reactor liquid phase by means of a sparger.

The present invention further provides a method of producing a carbonic ester by allowing an alcohol to react with carbon monoxide and oxygen in a liquid phase to provide the corresponding carbonic ester which comprises subjecting the gas from the reactor vapor phase to gas-liquid separation and recycling the non-condensible gas fraction to the reactor liquid phase to control the reaction temperature.

An alcohol having 1 to 6 carbon atoms can be used as said alcohol.

The reaction may be carried out in the presence of a palladium or copper catalyst. The non-condensable gas may contain not less than 25% by volume of an inert gaseous component such as carbon dioxide, nitrogen and so on.

DETAILED DESCRIPTION OF THE INVENTION

Figure 1:
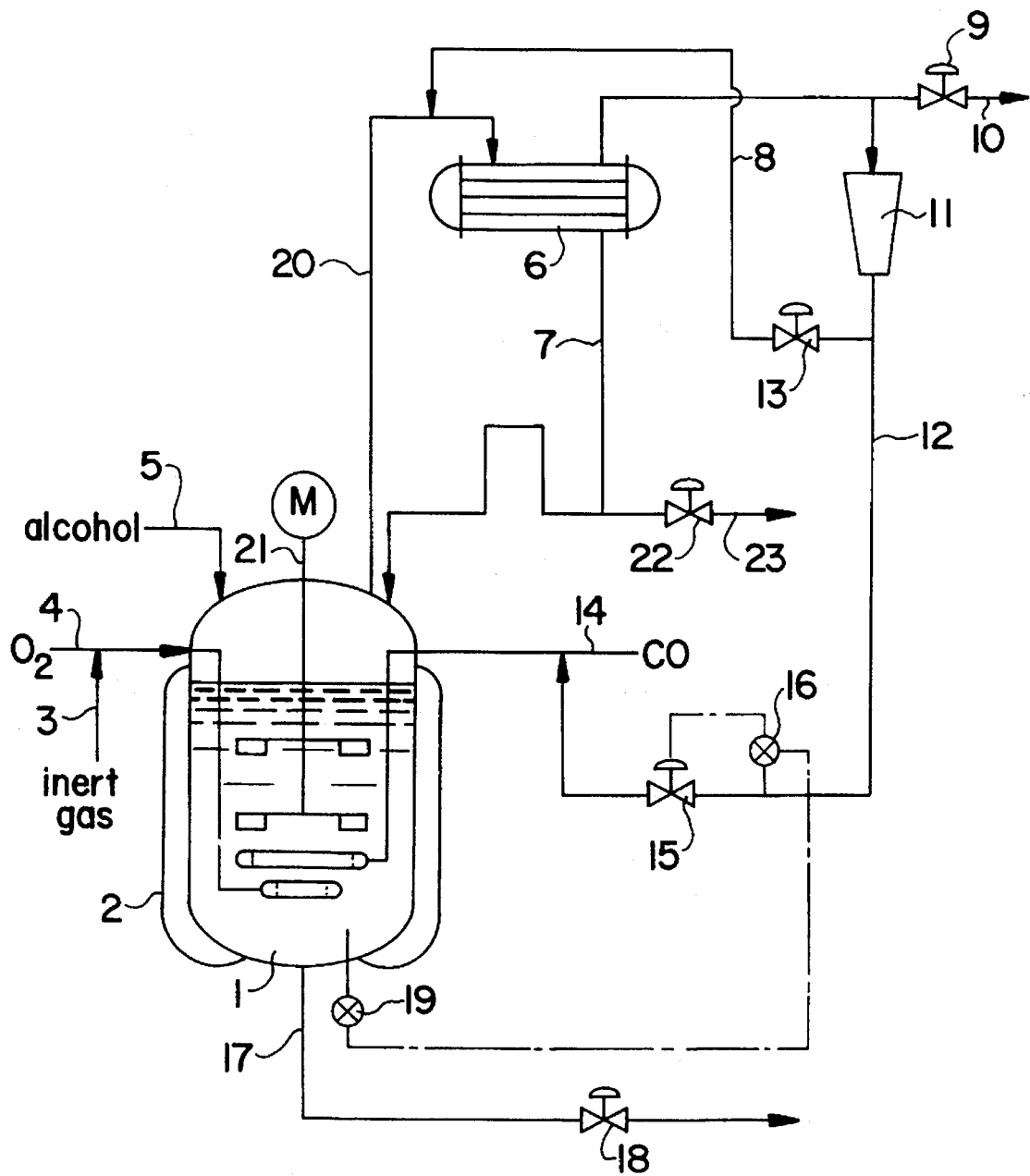
FIG. 1 is a schematic diagram showing the reactor used in the Examples.

The present invention is now described in further detail, reference being made to the accompanying drawing where necessary.

Referring to the method of controlling the reaction in accordance with the present invention, the subject reaction is not limited in type provided that it is a liquid-phase reaction involving a gaseous reactant and a liquid reactant and accompanied by the evolution of heat. The gaseous reactant mentioned above is not limited provided that it is a substance which can be separated as gas in the gas-liquid separation.

The reaction mentioned above comprises a reaction involving a gas such as oxygen, carbon monoxide or hydrogen as a reactant, including but not limited to Wacker oxidation and other reactions each giving a carbonyl compound through oxidation of an olefin; the so-called oxo reaction giving an aldehyde from an olefin, carbon monoxide and hydrogen; the reaction giving a carboxylic acid or a carboxylic anhydride from an alcohol and/or its ester and carbon monoxide (for example, the reaction giving acetic acid from methanol and carbon monoxide); the reaction giving a carboxylic acid and a carboxylic anhydride from at least two members selected from among an alcohol, a dialkyl ether and an alkyl ester and carbon monoxide (for example, the reaction giving acetic acid and acetic anhydride from methanol, methyl acetate and carbon monoxide); the reaction giving a carbonic ester from an alcohol, carbon monoxide and oxygen; and the reaction giving vinyl acetate from ethylene, acetic acid and oxygen in a liquid phase. The preferred reactions are those involving carbon monoxide and/or oxygen as gaseous reactants. Especially, the reactions using carbon monoxide and oxygen as gaseous reactants, for example the carbonic ester-synthesizing reaction involving an alcohol, carbon monoxide and oxygen as reactants are more preferable.

In the reaction giving a carbonyl compound through oxidation of an olefin, oxygen-containing gas such as oxygen and air is used as the gaseous reactant. The reaction is generally carried out by charging an olefin and oxygen-containing gas into an aqueous hydrochloric acid solution containing a catalyst comprising palladium chloride and where necessary cupric chloride or the like. The reaction temperature is generally about 50° to 150° C., and the reaction pressure is generally about 1 to 10 atm. According to the reaction, acetaldehyde can be produced from ethylene and oxygen, for instance.

Carbon monoxide and hydrogen are used as the gaseous reactants in the so-called oxo reaction. The reaction can be carried out at a pressure of about 1 to 300 atm and a temperature of about 10° to 200° C. The reaction may be conducted in an inert solvent such as toluene. Cobalt catalyst ([HCo(CO)$_4$] etc.), nickel catalyst ([Ni(CO)$_4$] etc.), iron catalyst ([H$_2$Fe(CO)$_4$] etc.), rhodium catalyst ([RhH(CO)(PPh$_3$)$_3$] etc.) or the like are used as the catalyst in this reaction. According to the above reaction, butyraldehyde and/or butyl alcohol are produced from propylene, carbon monoxide and hydrogen, for instance.

In the reaction giving a carboxylic acid or a carboxylic anhydride from an alcohol and/or its ester and carbon monoxide, carbon monoxide is used as the gaseous reactant. The reaction is conducted using a rhodium catalyst, cobalt catalyst or the like, particularly rhodium catalyst, as the catalyst. In the method of producing a carboxylic acid using a rhodium catalyst, an alcohol (for example methanol) and carbon monoxide are allowed to react in the reaction medium contaning the rhodium catalyst, alkyl iodide (for example methyl iodide), water and alkali metal halide (for example, lithium iodide etc.), in general. In the preferred embodiment of this method, the reaction is carried out in the liquid phase containing objective compound the carboxylic acid (for example acetic acid) and/or the corresponding carboxylic ester (for example methyl acetate), particularly the carboxylic ester. The reaction pressure is generally about 1 to 300 atm, preferably about 5 to 150 atm, and the reaction temperature is generally about 50° to 300° C., preferably about 150° to 250° C. In the preferred embodiment of this method, the concentration of iodide ion in the reaction medium is generally not less than 0.3 mole/L, preferably about 0.5 to 5 moles/L, and the concentration of water in the reaction medium is generally not more than 10% by weight, preferably about 1 to 10% by weight. The reaction conditions disclosed in the Japanese Patent Laid-open No. 54334/1985 are incorporated herein by reference. According to the above reaction, acetic acid can be produced efficiently from methanol and carbon monoxide, for instance.

In the reaction giving a carboxylic acid and a carboxylic anhydride from at least two members selected from among an alcohol, a dialkyl ether and an alkyl ester and carbon monoxide, carbon monoxide is used as the gaseous reactant. As the catalyst, rhodium, palladium, cobalt, nickel catalyst or the like, particularly rhodium catalyst, is used. The reaction pressure is generally about 1 to 300 atm and the reaction temperature is generally about 50° to 300° C. According to the above reaction, for example, acetic acid and acetic anhydride can be obtained from methanol, methyl acetate and carbon monoxide.

As the gaseous reactant, carbon monoxide and oxygen are used in the reaction giving a carbonic ester from an alcohol, carbon monoxide and oxygen. The reaction is conducted using a palladium halide, copper halide or the like as the catalyst.

Thus, many of catalysts used in the above liquid-phase reaction are strongly acidic or oxidative, hence are highly corrosive to metal hardware.

The reactant gas used in the above reactions need not be a high-purity gas but can be used as diluted with an inert gas such as nitrogen, helium, argon, carbon dioxide and so on. In any reaction using oxygen as one of starting materials, the material gas is preferably diluted with an inert gas to prevent formation of an explosive mixture. In such cases, air may be substituted for oxygen so that nitrogen in the air may be utilized as the inert gas. Furthermore, a by-product formed in the course of reaction, such as carbon dioxide gas, may be used as the diluent inert gas.

The reaction mode may be continuous, semi-continuous or batchwise. The reactor may also be of the positive agitation type or of the bubbling type.

As a typical example of the exothermic liquid-phase reaction wherein a liquid reactant reacts with a gaseous reactant, the carbonic ester-synthesizing reaction involving an alcohol, carbon monoxide and oxygen as reactants is now described in detail.

The alcohol mentioned above is a compound containing one or more hydroxyl groups within the molecule, thus including saturated aliphatic alcohols such as methanol, ethanol, 1-propanol, 2-propanol, 1-butanol, etc.; unsaturated aliphatic alcohols such as allyl alcohol; alicyclic alcohols such as cyclohexanol; aromatic alcohols such as benzyl alcohol and phenol; and polyhydric alcohols such as ethylene glycol and polyethylene glycol. The term 'aromatic alcohol' is used herein to include a variety of phenols containing a phenolic hydroxyl group. The preferred species of alcohol are monohydric saturated or unsaturated alcohols, such as alcohols of about 1 to 6 carbon atoms. Among the most preferred species of alcohol are methanol and ethanol, and methanol is generally the alcohol of choice.

The reaction can be conduced in an inert solvent. The solvent mentioned just above includes, among others, ketones such as acetone; ethers such as diethyl ether, dimethoxyethane and tetrahydrofuran; carboxylic acids such as formic acid, acetic acid and propionic acid; esters such as methyl acetate; amides such as N,N-dimethylformamide; nitriles such as acetonitrile; aliphatic hydrocarbons such as hexane and octane; alicyclic hydrocarbons such as cyclohexane; aromatic hydrocarbons such as benzene, toluene and xylene; and halogenated hydrocarbons such as dichloromethane and 1,2-dichloroethane. The reactant alcohol and/or the objective carbonic ester may also be utilized as the solvent. These solvents can be used independently or in combination.

The catalyst for the above reaction is not particularly critical. For example, a copper catalyst containing a copper compound as the main catalyst component or a platinum-group metal catalyst containing a platinum-group metal compound such as a palladium compound as the main catalyst component can be employed.

When a copper catalyst is employed, the preferred copper compound includes monovalent or divalent copper halides such as chloride and bromide; alkoxyhalides such as methoxychloride; inorganic acid salts such as sulfate, nitrate and carbonate; organic acid salts such as acetate and pivalate; oxide; and hydroxide. These copper compounds can be used independently or in combination. The amount of the copper compound as the catalyst is generally about 0.01 to 20 moles/L and preferably about 0.1 to 10 moles/L.

The referred promotor for such a copper catalyst includes tertiary amines, amidines, alkali metal alkoxides, alkylphosphines, pyridines, imidazoles, phosphoramides and cyclic urea derivatives. Cyclic urea derivatives can be used as the solvent as well.

As the platinum-group metal catalyst, a palladium catalyst comprising a palladium compound as the main catalyst and a weak acid salt or halide of copper and a weak acid salt or halide of an alkali metal or alkaline earth metal as the promoter can be used with advantage.

The palladium compound mentioned above includes, among others, halides, e.g. fluoride, chloride and bromide, of palladium; salts of palladium with organic acids such as acetic acid, propionic acid, trifluoroacetic acid, formic acid, citric acid, methanesulfonic acid, benzenesulfonic acid and p-toluenesulfonic acid; and salts of palladium with inorganic acids such as sulfuric acid and nitric acid. The preferred palladium compound is a palladium halide, particularly palladium chloride. The amount of the palladium compound as the main catalyst component may for example be about 0.0001 to 0.1 mole/L, preferably about 0.001 to 0.01 mole/L.

The above-mentioned salts of copper with weak acids include salts with organic acids such as acetic acid, propionic acid, pivalic acid, formic acid, lactic acid, citric acid and benzoic acid; salts with inorganic acids such as boric acid and carbonic acid; and salts with phenols such as phenol and cresol. The halide of copper includes, among others, cuprous chloride, cupric chloride, cuprous bromide and cuptic bromide. Of these copper compounds, the salt of divalent copper with an organic acid, for example cupric acetate, as well as cupric chloride can be generally used with advantage. These copper compounds can be used independently or in combination.

The amount of the weak acid salt or halide of copper can be selected from a broad range and may for example be about 0.0001 to 10 moles/L, preferably about 0.001 to 1 mole/L.

The alkali metal mentioned above includes lithium, sodium, potassium, rubidium, cesium and so on. The alkaline earth metal includes beryllium, magnesium, calcium, barium and so on.

The salts of such alkali metal or alkaline earth metal with weak acids include salts with said organic acids, inorganic acids and phenols. The halide of alkali metal or alkaline earth metal includes the corresponding fluoride, chloride, bromide and so on. Among these alkali metal or alkaline earth metal compounds, organic acid salts, e.g. acetates, and chlorides are generally employed. The alkali metal or alkaline earth metal compounds can be used independently or in combination.

The alkali metal or alkaline earth metal compound mentioned above inhibits the conversion of carbon monoxide to carbon dioxide and enhances the selectivity for the carbonic ester. The amount of the alkali metal or alkaline earth metal compound may for example be about 0.1 to 1000 moles, preferably about 10 to 200 moles, per mole of said copper compound.

Referring, again, to the above-mentioned palladium catalyst, at least one of its component palladium compound, copper compound and alkali metal or alkaline metal compound preferably contains halogen.

Where both copper and halogen atoms are present in the catalyst, the atomic ratio of halogen to copper (Hal/Cu ratio) is preferably about 0.5 to 2 and more preferably about 1.5 to 1.8. The Hal/Cu ratio has an important bearing on the velocity of the reaction. Thus, any Hal/Cu ratio of less than 0.5 results in a decreased solubility of copper, while any Hal/Cu ratio over 2 results in a considerable decrease in reaction velocity.

The reaction pressure can be any pressure within the range wherein the reaction efficiency is not adversely affected and the formation of by-products is minimal. As such, the reaction pressure may, for example, be generally about 5 to 50 $Kg/cm^2$ and preferably about 15 to 40 $Kg/cm^2$.

The carbon monoxide partial pressure can be selected from the range where a sufficiently high reaction velocity can be insured. For example, the CO partial pressure is preferably about 0.5 to 47 $Kg/cm^2$ when the reaction is conducted in the presence of a copper catalyst and about 0.5 to 5 $Kg/cm^2$ for the reaction in the presence of a palladium catalyst.

The oxygen partial pressure is not critical but is generally selected from the range where an explosive mixture will not be formed. Thus, the $O_2$ partial pressure may for example be generally about 0.05 to 10 $Kg/cm^2$ and preferably about 0.05 to 5 $Kg/cm^2$.

The reaction temperature can be selected from the range which does not lower the reaction velocity and inhibits the by-production of oxalic ester. Thus, it may for example be generally about 50° to 200° C. and preferably about 100° to 150° C. When the reaction temperature is too low, the reaction velocity is lowered and the relative yield of by-product oxalic ester and the like is increased. Conversely when the reaction temperature is too high, the vapor pressure of the reaction mixture is elevated and the total pressure is accordingly increased. This is disadvantageous in that the operation requires a costly pressure-resistant reactor, which is an economic drawback.

In the above manner, a carbonic ester is produced from the corresponding alcohol, carbon monoxide and oxygen.

It is an outstanding feature of the present invention that the reaction temperature is controlled by a simple procedure comprising subjecting the reactor vapor phase gas to gas-liquid separation and recycling the non-condensible gas fraction to the reactor liquid phase.

The gas-liquid separation of the reactor vapor phase gas can be achieved by cooling the vapor phase gas in a heat-exchange device such as a condenser. In the production of a carbonic ester by said carbonic ester-synthesizing reaction, for instance, this gas-liquid separation can be achieved by cooling the vapor phase gas to a temperature, for example about −10° to 50° C., where the starting material alcohol, product carbonic ester and by-product water are condensed under the reaction pressure.

For enhancing the efficiency of gas-liquid contact and increasing the surface area of bubbles to thereby improve the efficiency of cooling due to the latent heat of vaporization, it is a preferred procedure to increase the pressure of said non-condensible gas with a compressor and sparge the pressurized gas through the reactor liquid phase. The reaction temperature can be controlled efficiently regardless of reactor volume by sparging the non-condensible gas through the reactor liquid phase.

As the reactor liquid phase is supplied with the non-condensible gas from the gas-liquid separator, the reaction mixture is not only cooled by the supplied gas which has been cooled in the gas-liquid separator but also cooled by the latent heat of vaporization of the liquid components [in the case of said carbonic ester-synthesizing reaction, starting material alcohol, product carbonic ester, etc.] in the reactor liquid phase. Therefore, the reaction temperature can be successfully controlled by recycling said non-condensible gas to the reactor liquid phase.

The amount of heat generated by the reaction is now designated as $\Delta H_1$, the amount of heat removed upon heat radiation, withdrawal of the reaction mixture from the reactor and the like even when the non-condensible gas is not recycled is designated as $\Delta H_2$, and the amount of heat removed upon recycling of non-condensible gas to the liquid phase is designated as $\Delta H_3$. Then, the following equation holds for the steady state at a given reaction temperature.

$$\Delta H_1 = \Delta H_2 + \Delta H_3$$

Meanwhile, $\Delta H_3$ varies according to the temperature and amount of non-condensible gas recycled. Therefore, the reaction temperature can be controlled either by controlling the flow rate of the non-condensible gas recycled to the reactor liquid phase or by controlling the temperature of said non-condensible gas.

Control of the amount of the non-condensible gas recycled from the gas-liquid separator can be carried out using a flow regulating valve. The degree of opening of the flow regulating valve can be adjusted manually but is preferably regulated automatically. On the automatic mode, the reaction temperature can be controlled more easily and accurately. In an automatic operation, the proportionality of the degree of cooling to the amount of the non-condensible gas recycled can be exploited. This automatic control of the flow rate of non-condensible gas recycled to the reactor liquid phase can be carried out using a feedback controller. This feedback controller comprises a temperature detecting means, such as a temperature sensor, which detects the reaction temperature within the reactor, a calculating means for calculating the controlled variable to a reference value set according to the desired reaction temperature (i.e. the amount of deviation) from the value detected by said temperature detecting means and said reference value, and a control means which, in response to a control signal corresponding to the controlled variable from said calculating means, controls the period or degree of opening of said regulating valve for example electromagnetic valve and diaphragm valve and thereby control the recycling amount of non-condensible gas.

When the detected reaction temperature value increases beyond the reference value, the amount of non-condensible gas recycled to the reactor liquid phase is increased and conversely when the detected value decreases below the reference value, the recycling amount is decreased so as to control the reaction temperature.

When a compressor is installed in the non-condensible gas circuit, a bypass line is preferably installed between the upstream and downstream sides of the compressor. When such a bypass line is provided, any surplus of the gas compressed in the compressor flows into the bypass line to permit a very smooth control of gas flow and, hence, an easy and accurate control of the reaction temperature.

The flow rate at which the non-condensible gas is recycled cannot be stated in general terms, for it varies with the type of reaction, species and amounts of reactants, target reaction temperature, the amount of withdrawal of the reaction mixture, reactor capacity and geometry, temperature of non-condensible gas, and whether the condensate is recycled to the reactor or not. However, in the production of a carbonic ester by said carbonic ester-synthesizing reaction, for instance, the flow rate of non-condensible gas may for example be generally about 0.5 to 5 $Nm^3/H$ and preferably about 0.8 to 3 $Nm^3/H$, per L of the reaction mixture.

Control of the temperature of said non-condensible gas can be effected by regulating the temperature and/or flow rate of a cooling medium supplied to the heat exchanger installed in the non-condensible gas circuit. The same object can also be accomplished by regulating the temperature of the cooling medium in the heat exchanger used for the gas-liquid separation of the reactor vapor phase gas. Just as in the control of the recycling flow rate of non-condensible gas, the temperature or flow rate of said heat-exchanger cooling medium can be controlled either manually or automatically.

Since the effect of cooling by said latent heat of vaporization is considerably great, the reaction temperature is effectively controlled by regulating the flow rate of non-condensible gas recycled. Control of the reaction temperature can also be carried out by using the above-mentioned flow rate control and temperature control for non-condensible gas in combination. This combination of flow rate and temperature controls for non-condensible gas provides for a quick reaction to any sudden upsurge in the internal temperature of the reactor and permits a delicate temperature control to thereby allow the objective product to be produced with good reproducibility.

The composition of the non-condensible gas to be recycled to the reactor liquid phase depends on the type of reaction, type of catalyst and other conditions of reaction and cannot be defined in general terms. From the standpoint of the ease of control of reaction temperature, however, the concentration of inert gaseous components not participating in the reaction is for example not less than about 25% by volume, preferably not less than about 40% by volume and more preferably not less than about 60% by volume (for example about 70 to 99% by volume). In the production of a carbonic ester by said carbonic ester-synthesizing reaction using a palladium catalyst, for instance, it is advisable to insure that the total concentration of the reactant oxygen and carbon monoxide will be less than 40% by volume, while the total concentration of reaction-inert gaseous components, e.g. carbon dioxide and nitrogen, will be not less than 60% by volume. Furthermore, the particularly preferred composition of the non-condensible gas to be recycled in the above reaction is about 0.1 to 10% by volume of oxygen, about 0.1 to 20% by volume of carbon monoxide and about 70 to 99% by volume of carbon dioxide and other inert gases.

The composition of the gas to be recycled can be analyzed, for example by gas chromatography. By such analysis of gas composition, the proper charge rates of starting materials such as oxygen and carbon monoxide can be determined.

Furthermore, in the method of the invention, a buffer tank for said non-condensible gas may be advantageously installed in the non-condensible gas circuitry and, when a compressor is installed in the circuitry, particularly in the upstream side of the compressor. The provision of such a buffer tank is advantageous in that even when the internal temperature of the reactor rises sharply to necessitate a substantial increase in the flow rate of the non-condensible gas, the reaction temperature can be quickly and accurately controlled without disturbing the reaction system by utilizing the non-condensible gas in the buffer tank having large volume. Moreover, the unreacted starting materials can be utilized with a very high efficiency. The non-condensible gas inlet of said buffer tank may be provided with a check valve to prevent the non-condensible gas flow backward from the buffer tank to the heat-exchanger for the gas-liquid separation. Moreover, the buffer tank may be of the cylinder type. When a cylinder-type buffer tank is employed, the volume of the buffer tank changes according to the change of pressure, so that the reaction temperature can be controlled while the reaction system pressure is held steady, and the objective compound can be produced in good yield and steadiness.

Furthermore, in the method of the invention, the reactor may be provided with an inert gas supply line equipped with a flow control valve. The provision of such an inert gas supply line is advantageous in that even if the change in reaction temperature is so sudden and great that it cannot be successfully followed up by a mere adjustment of the flow rate and/or temperature of said non-condensible gas, the reaction temperature can be quickly and easily controlled by regulating the period or degree of opening of said flow control valve. Though the period or degree of opening of said flow control valve can be regulated manually or automatically, an automatic valve operation is preferred. This automatic valve operation can be effected by a feedback controller such as the one mentioned hereinbefore.

Since the method of the invention comprises subjecting the reactor vapor phase gas to gas-liquid separation and recycling the non-condensible gas fraction to the reactor liquid phase, unlike the case in which the reaction temperature is controlled by recycling the reaction mixture containing the corrosive catalyst, it is unnecessary to use expensive corrosion-resistant structural materials and the reaction temperature can be controlled with simple hardware and software. Moreover, unlike the case in which a cooling medium is circulated through the reactor jacket, the cracking and peeling of the anticorrosive internal lining of the reactor can be prevented.

Furthermore, since the cooled gas is bubbled through the reactor liquid phase, an improved efficiency of heat removal is realized and the object temperature control is also facilitated.

In addition, while the non-condensible gas contains unreacted gaseous starting materials, these starting materials can be effectively utilized not only in the reaction but also for control of the reaction temperature. Moreover, in cases where an inert gas is by-produced as the result of reaction, it can be utilized as the diluent gas. Taking the production of a carbonic ester by said carbonic ester-synthesizing reaction as an example, the non-condensible gas contains not only the by-product carbon dioxide but also the unreacted carbon monoxide and oxygen. Therefore, by bubbling this non-condensible gas through the reactor liquid phase, the by-product carbon dioxide gas can be utilized as the diluent gas and, in addition, both the yield of the carbonic ester and the rates of utilization of carbon monoxide and oxygen can also be improved. Therefore, the method of the invention offers a remarkable commercial advantage.

The present invention can be applied with particular advantage to a continuous production line in which a reactor is continuously supplied with a reactant mixture containing a catalyst and the reaction mixture and gases are continuously withdrawn from the reaction system.

The reaction mixture withdrawn is purified by the routine procedure such as distillation, solvent extraction and the like to isolate the objective compound. Taking said carbonic ester-synthesizing reaction as an example, the carbonic ester corresponding to the starting material alcohol is produced in the manner described above.

The unreacted starting materials in the reaction mixture withdrawn from the reaction system can be recycled, together with the catalyst, to the reaction system. Moreover, the condensate obtained by gas-liquid separation, which contains the liquid reactant (e.g. alcohol) and reaction product (e.g. carbonic ester), can also be recycled to the reaction system. In this manner, the yield of the objective compound (e.g. carbonic ester) is further enhanced.

FIG. 1 is a schematic diagram illustrating an exemplary continuous reaction system. Illustrated is the reactor used in Examples, which appear hereinafter, where a carbonic ester is produced by said carbonic ester-synthesizing reaction.

A reactor 1 is fitted with a heating medium jacket 2 for heating the charge to a predetermined temperature for initiation of the operation. Further connected to said reactor 1 are a first supply line 5 for feeding the starting material alcohol via a metering pump and the like, a second supply line 4 for feeding oxygen, a third supply line 3 for feeding an inert gas, and a fourth supply line 14 for feeding carbon monoxide.

Through the first supply line 5, the alcohol containing a catalyst at a predetermined concentration is continuously introduced into the reactor 1. The second and third supply lines converge partway and extend into the liquid phase within the reactor 1 for an improved efficiency of gas-liquid contact. The flow rates of oxygen, carbon monoxide and inert gas are respectively controlled by valve means. The reactant gases and inert gas in predetermined proportions are generally sparged through the liquid phase by means of a sparger for an improved gas-liquid contact efficiency. By sparging the gases by means of the sparger, the reaction temperature can be controlled efficiently regardless of reactor volume.

The reactor 1 is further equipped with an agitator 21. In the illustrated example, a plurality of disk-turbine blades are used for improved gas-liquid contact efficiency.

Further connected to the reactor 1 is a withdrawal line 17 for withdrawal of the reaction mixture, said withdrawal line 17 communicating with the reactor liquid phase and including a liquid level valve 18 for adjusting the liquid level by continuous withdrawal of the reaction mixture.

Further connected to the reactor 1 is a gas withdrawal line 20 communicable to the reactor gas phase. This line 20 is provided with a condenser 6 and a pressure regulating valve 9. The condensate obtained by said condenser 6 is recycled through a condensate return line 7 to the reactor 1. It is so arranged that a portion or the whole of the condensate can be transferred to the downstream carbonic ester purification stage via a flow control valve 22 and a condensate withdrawal line 23.

The gaseous fraction, which was not condensed in the said condenser 6, is compressed by a compressor 11 and recycled, together with carbon monoxide, to the reactor 1 through a recycle gas charge line 12 and said forth supply line 14 with which the line 12 converges pathway. The amount of the gas to be recycled is controlled by regulating the degree of opening of a recycle gas flow regulating valve 15 in such a manner that a flow rate (as detected by a flowmeter 16) necessary to maintain the reaction temperature (the reading of a thermometer 19 disposed in the reactor) at a predetermined value will be obtained. This control is carried out using a feedback controller comprising a thermometer 19 which detects the reaction temperature within the reactor, a calculating circuit for calculating the controlled variable to a reference value set according to the desired reaction temperature (i.e. the amount of deviation) from the value detected by said thermometer and said reference value, and a control circuit which, in response to a control signal corresponding to the controlled variable from said calculating circuit, controls the degree of opening of said regulating valve 15.

Of the gas compressed by the compressor 11, the balance which is not recycled to the reactor 1 is returned to said gas withdrawal line 20 through a mini-flow control valve 13 and a recycle gas mini-flow line 8. A portion of the gas fraction not condensed by said condenser 6 is exhausted from the reaction system via an off gas line 10 through the pressure regulating valve 9 in order to maintain the reaction pressure at a constant level.

It should be understood that the line for recycling the condensate to the reactor, recycle gas mini-flow line 8, etc. are not essential to the method of the invention.

In the method of control according to the present invention, the non-condensible gas fraction of the reactor vapor phase gas is recycled to the reactor liquid phase at a controlled flow rate and/or temperature to thereby control the reaction temperature, with the result that even in the presence of a highly corrosive catalyst, the reaction temperature can be easily controlled with simple hardware and software. Moreover, since the gaseous reactants contained in the non-condensible gas are recycled to the reaction system, the rates of utilization of the reactants are improved. In addition, the reaction temperature can be controlled efficiently regardless of reactor volume since the gasseous components are introduced into the reactor liquid phase.

Furthermore, in the production method of the present invention, the non-condensible gas fraction of the reactor vapor phase gas, which contains carbon monoxide, oxygen, by-product carbon dioxide and the like, is recycled to the reactor liquid phase and the reaction temperature is controlled by regulating the flow rate or the like of this recycle gas. Therefore, the reaction temperature can be easily controlled without resort to any complicated equipment and procedure and, yet, a stable production of the carbonic ester can be realized even when a highly corrosive catalyst is present in the reaction system.

Furthermore, the rates of utilization of carbon monoxide and oxygen and the yield of carbonic ester are all improved and the by-product carbon dioxide can be effectively utilized.

The following examples are intended to describe the present invention in further detail and should by no means be interpreted as defining the scope of the invention.

EXAMPLES

Example 1

A 200-liter capacity glass-lined pressure-resistant reactor equipped with a two-stage disk type turbine blades was continuously supplied with a methanolic solution containing 0.51 mmole/L of palladium chloride, 50.25 mmoles/L of cupric chloride, 6.75 mmoles/L of cupric acetate, 57 mmoles/L of magnesium acetate and 25.5 mmoles/L of acetic acid at a flow rate of 150 L/H. At the same time, the reactor was supplied with 12.9 Nm$^3$/H of carbon monoxide, 6.4 Nm$^3$/H of oxygen and 2.0 Nm$^3$/H of nitrogen through a sparger at bottom. The reaction was started at a temperature of 130° C.

To control the liquid volume in the reactor at 75L, the liquid level was controlled by withdrawing the reaction mixture continuously from the liquid level valve disposed at the reactor bottom.

The gas emerging from the reactor was fed under pressure to a stainless steel two-phase condenser to separate a condensible fraction containing methanol, dimethyl carbonate and water and the non-condensible gas fraction was compressed with a compressor and recycled to the reactor at a flow rate of 74.0 Nm$^3$/H which was necessary for removal of heat to maintain the reaction temperature at 130° C. The temperature of the compressor exit gas was 36° C.

In order that the reaction pressure could be maintained at 21 Kg/cm$^2$G, a portion of the non-condensible gas was exhausted from the pressure regulating valve at a flow rate of 9.2 Nm$^3$/H.

TO prevent formation of an explosive mixture, the concentrations of oxygen and carbon monoxide in the gas withdrawn via the pressure regulating valve were monitored using an oxygen analyzer and a gas chromatograph and the supply rates of oxygen and carbon monoxide to the reactor were accordingly regulated. In steady-state operation, the above-mentioned gas supply rates were constant and, in the exhaust gas, the concentration of oxygen was 4% by volume and that of carbon monoxide was 1.4% by volume, with carbon dioxide and nitrogen accounting for the balance.

The methanol, dimethyl carbonate and water condensed by said condense were returned to the reactor in the manner of spontaneous dripping through a U-shaped liquid seal pipe.

Of the methanol fed to the reactor, 15.9% was converted to dimethyl carbonate.

Under the above conditions, the amount of heat $\Delta H_1$ produced by the reaction was 40.9 kkcal/H and the amount of heat $\Delta H_2$ removed on heat radiation from the reactor and withdrawal of the reaction mixture even without recycling of non-condensible gas was 20.1 kkcal/H. The heat corresponding to the difference of 20.8 kkcal/H between $\Delta H_1$ and $\Delta H_2$ was removed by recycling said non-condensible gas to the reactor liquid phase at a flow rate of 74.0 Nm$^3$/H so that the reaction temperature could be controlled at a constant level.

Example 2

Except that the condensate containing methanol, dimethyl carbonate and water was not returned to the reactor but withdrawn at a flow rate of 81 L/H and transferred to the downstream dimethyl carbonate isolation stage, the reaction procedure of Example 1 was otherwise repeated.

The non-condensible gas was recycled to the reactor liquid phase at a flow rate of 85.4 Nm$^3$/H to maintain the reaction mixture at 130° C. The amount of heat $\Delta H_1$ generated by the reaction was 40.9 kkcal/H, the amount of heat $\Delta H_2$ removed on heat radiation from the reactor and withdrawal of the reaction mixture even without recycling of non-condensible gas was 16.9 kkcal/H, and the amount of heat $\Delta H_3$ removed by the recycled gas was 24.0 kkcal. This thermal balance maintained the reaction temperature at the above constant level.

What is claimed is:

1. A method of producing a carbonic ester by allowing methanol to react with carbon monoxide and oxygen in a liquid phase to provide the corresponding dimethyl carbonate which comprises supplying continuously the reactants and a catalyst to a reactor wherein a reactor liquid phase and a reactor vapor phase are obtained, subjecting at least a portion of said reactor vapor phase gas to gas-liquid separation to obtain a condensable gas fraction and a non-condensable gas fraction, controlling the temperature of the reaction within the range of about 100° C. to about 150° C. by recycling at least a portion of said non-condensable gas fraction to said reactor liquid phase and sparging said reactor liquid phase with said portion of recycled non-condensable gas fraction, wherein the flow rate of the recycled gas is regulated within the range of 0.5 to 5 Nm$^3$/H per liter of the reaction mixture, and withdrawing continuously an amount of the reactor liquid phase to adjust the liquid level in the reactor.

2. The method according to claim 1, wherein the oxygen and carbon monoxide are supplied in admixture with at least one inert gas, and said non-condensable gas fraction contains not less than 25% by volume of inert gas.

3. The method according to claim 2, wherein the portion of said non-condensable gas fraction recycled to said reactor liquid phase for sparging contains 0.1 to 10% by volume of oxygen, 0.1 to 20% by volume of carbon monoxide, and 70 to 99% by volume of inert gas.

4. A method according to claim 1, wherein said reaction is conducted in the presence of a palladium or copper catalyst.

5. A method according to claim 4, wherein said method further comprises compressing at least a portion of said non-condensable gas fraction and said non-condensable fraction contains not less than 25% by volume of an inert gas.

6. The method according to claim 5, wherein said method further comprises controlling the flow rate of the recycled gas with a feedback controller.

7. The method according to claim 5, wherein said method only a portion of the compressed and non-condensable gas fraction is recycled to said reactor liquid phase, and at least a portion of the remaining compressed and non-condensable gas fraction is recycled to a gas withdrawal line in communication with said reactor vapor phase.

8. The method according to claim 5, wherein said method further comprises storing the non-condensable gas before recycling all or a portion thereof to said reactor liquid phase.

9. The method according to claim 5, wherein the amount and rate of withdrawal of the portion of the reactor liquid phase is such that the amount of dimethyl carbonate withdrawn is substantially equal to the amount thereof formed in the reactor.

10. A method for producing dimethyl carbonate in a reactor by allowing methanol to react with oxygen and carbon monoxide in a liquid phase which comprises supplying continuously (i) carbon monoxide, oxygen and at least one inert gas, wherein the oxygen is present in an amount sufficient to have an oxygen partial pressure of that of 0.05 to 10 kg/cm$^2$ relative to the gases supplied, and the total concentration of the oxygen and carbon monoxide is less than 40% by volume relative to the gases supplied, (ii) a catalyst containing a main component, said main component containing a metal selected from the group consisting of copper and palladium, and (iii) methanol to said reactor whereby a reaction mixture having a reactor liquid phase and a reactor vapor phase is obtained, condensing a portion of said reactor vapor phase to form a condensable fraction and non-condensable fraction wherein the condension comprises cooling said portion of said reactor vapor to a temperature of about −10° C. to 50° C.;

recycling at least a portion of said non-condensable fraction to said reactor and sparging reactor liquid phase with said recycled portion, controlling the temperature of said reaction within the range of about 100° C. to about 150° C. by regulating the flow rate of the recycled non-condensable fraction of about 0.5 to 5 Nm$^3$/H per liter of said reaction mixture, and adjusting the liquid level of said reactor by withdrawing continuously an amount of the reactor liquid phase, wherein said reaction is conducted at a pressure of about 5 to 50 kg/cm$^2$.

11. A method according to claim 10, wherein the carbon monoxide is supplied in an amount sufficient to have a carbon monoxide partial pressure of about 0.5 to 5 kg/cm$^2$.

12. A method according to claim 10, wherein the carbon monoxide is supplied in an amount sufficient to have a carbon monoxide partial pressure of about 0.5 to 47 kg/cm$^2$.

13. A method according to claim 10, wherein the oxygen is supplied in an amount sufficient to have an oxygen partial pressure of about 0.05 to 5 kg/cm$^2$.

14. A method according to claim 10, wherein said catalyst contains at least one palladium-containing main component wherein the palladium-containing main component is present in a concentration of 0.0001 to 0.1 mol/liter.

* * * * *